United States Patent
Zhang et al.

(10) Patent No.: US 9,561,030 B2
(45) Date of Patent: Feb. 7, 2017

(54) SURGICAL STAPLE AND STAPLE POCKET FOR FORMING KIDNEY-SHAPED STAPLE

(75) Inventors: Zuren Zhang, Shanghai (CN); Wei Min Yang, Changzhou (CN); Suying Li, Changzhou (CN); Zhenyu Jiang, Changzhou (CN); Dongkun Yuan, Changzhou (CN); Guoan Yu, Changzhou (CN); Rong Ji, Changzhou (CN); Yiyi Zhang, Shanghai (CN); Weihua Xu, Shanghai (CN)

(73) Assignees: CHANGZHOU KANGDI MEDICAL STAPLER CO., LTD., Xinbei District Changzhou, Jiangsu (CN); SHANGHAI CHUANGYI MEDICAL DEVICE TECH. CO., LTD., Pudong District, Shanghai (CN)

( * ) Notice: Subject to any disclaimer, the term of this patent is extended or adjusted under 35 U.S.C. 154(b) by 522 days.

(21) Appl. No.: 14/125,070

(22) PCT Filed: May 11, 2012

(86) PCT No.: PCT/CN2012/075325
§ 371 (c)(1),
(2), (4) Date: Dec. 9, 2013

(87) PCT Pub. No.: WO2012/171423
PCT Pub. Date: Dec. 20, 2012

(65) Prior Publication Data
US 2014/0110457 A1    Apr. 24, 2014

(30) Foreign Application Priority Data

Jun. 14, 2011  (CN) .......................... 2011 1 0158300
Jul. 18, 2011  (CN) .......................... 2011 2 0252204

(51) Int. Cl.
A61B 17/068    (2006.01)
A61B 17/064    (2006.01)
(Continued)

(52) U.S. Cl.
CPC ......... *A61B 17/068* (2013.01); *A61B 17/0644* (2013.01); *A61B 17/07207* (2013.01); *A61B 17/1155* (2013.01); *A61B 2017/07264* (2013.01)

(58) Field of Classification Search
USPC .......................... 227/19, 177.1, 178.1, 179.1
See application file for complete search history.

(56) References Cited

U.S. PATENT DOCUMENTS 5,221,036 A * 6/1993 Takase ................. A61B 17/072
                                                                 227/113
5,350,400 A * 9/1994 Esposito ............ A61B 17/0644
                                                                 227/902

(Continued)

*Primary Examiner* — Nathaniel Chukwurah
(74) *Attorney, Agent, or Firm* — Global IP Services; Tianhua Gu

(57) ABSTRACT

The present invention disclosed a surgical staple (50) and staple pocket (57) for forming kidney-shaped staple therefor, with the staple pocket (57) being recessed inward on the tissue contacting surface of the staple anvil (58), and with M-shaped staple (50) being used, wherein the degree of projection of the middle portion of the back span (51) of the M-shaped staple (50) arranged at the inner circle or arranged at a proximal side of a cutter slot (121) is larger than that of the back span (51) of the M-shaped staple (50) arranged at the outer circle or arranged at a distal side of the cutter slot (121), so that when the staple (50) of the same height are adapted to staple tissues to be stapled of different thickness, staple driver (68) bends the M-shaped staple (50) on the staple pocket (57) to form kidney-shaped staple (50) so as to (Continued)

achieve the operational effect of being able to seal the stapled tissue, to stop bleeding and to heal the tissue therearound.

11 Claims, 17 Drawing Sheets

(51) Int. Cl.
*A61B 17/072* (2006.01)
*A61B 17/115* (2006.01)

(56) References Cited

U.S. PATENT DOCUMENTS

| | | | | |
|---|---|---|---|---|
| 5,738,474 | A * | 4/1998 | Blewett | A61B 17/07207 |
| | | | | 411/473 |
| 5,915,616 | A * | 6/1999 | Viola | A61B 17/072 |
| | | | | 227/175.1 |
| 2006/0124688 | A1* | 6/2006 | Racenet | A61B 17/0644 |
| | | | | 227/175.1 |
| 2006/0291981 | A1* | 12/2006 | Viola | A61B 17/0644 |
| | | | | 411/457 |
| 2009/0255978 | A1* | 10/2009 | Viola | A61B 17/07207 |
| | | | | 227/180.1 |
| 2011/0087276 | A1* | 4/2011 | Bedi | A61B 17/0644 |
| | | | | 606/219 |
| 2011/0226837 | A1* | 9/2011 | Baxter, III | A61B 17/0644 |
| | | | | 227/175.1 |

* cited by examiner

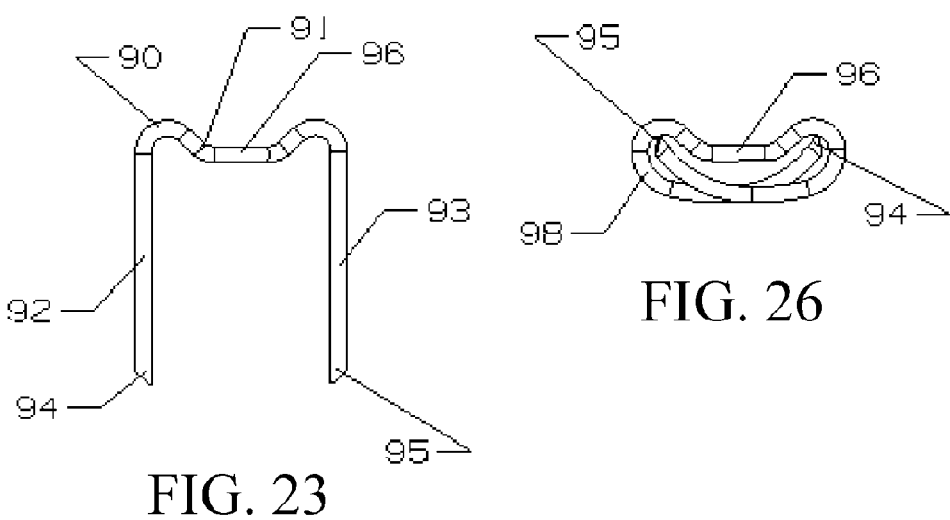
FIG. 23
FIG. 26
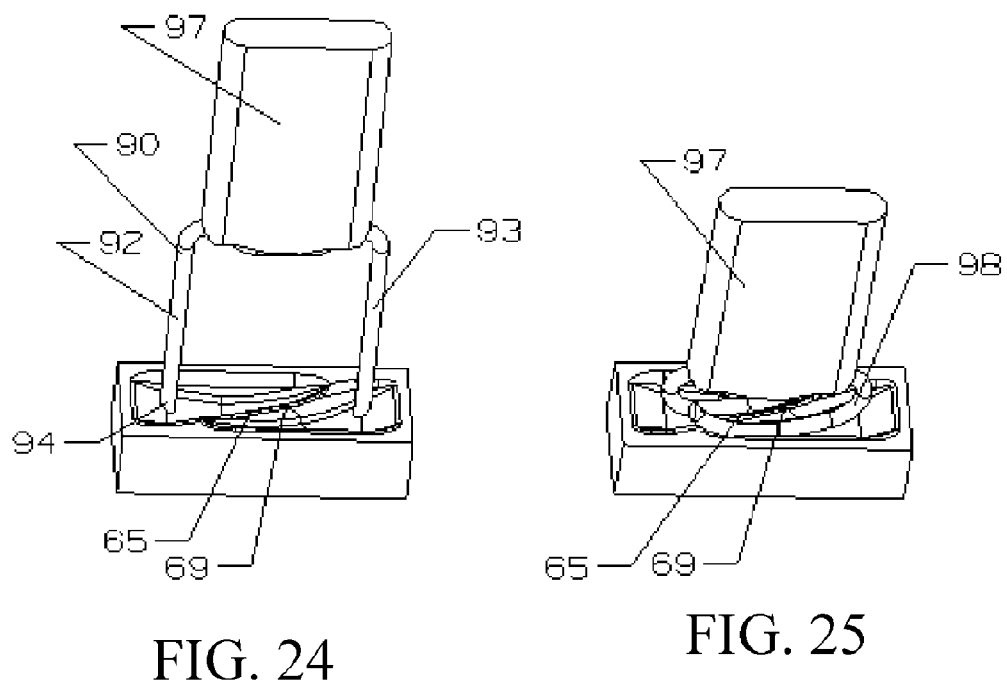
FIG. 24
FIG. 25

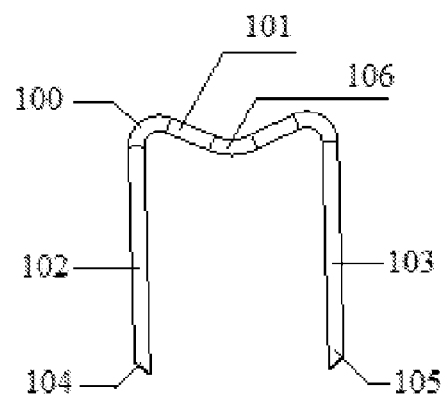
FIG. 30
FIG. 27
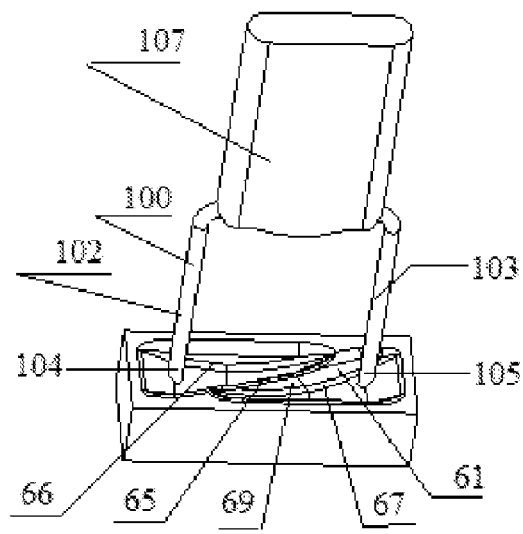
FIG. 28
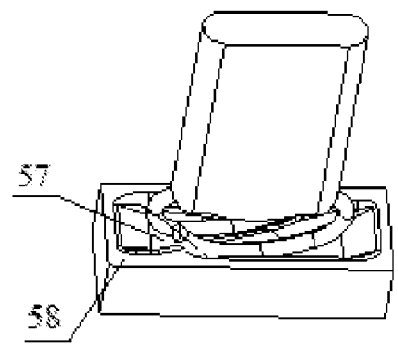
FIG. 29

SURGICAL STAPLE AND STAPLE POCKET FOR FORMING KIDNEY-SHAPED STAPLE

CROSS REFERENCE TO RELATED PATENT APPLICATION

The present application is the US national stage of PCT/CN2012/075325 filed on May 11, 2012, which claims the priorities of the Chinese patent applications No. 201110158300.9 filed on Jun. 14, 2011 and No. 201120252204.6 filed on Jul. 18, 2011, which applications are incorporated herein by reference.

BACKGROUND OF THE PRESENT INVENTION

Field of Invention

The present invention relates to surgical staples and staple pockets used in various surgical staplers, and more particularly to surgical staple and staple pocket for forming kidney-shaped staple.

Description of Related Arts

Various surgical staplers used for replacing needles and thread, for manual stapling, in surgery are widely used in surgery such as end-end, end-side, and side-side stapling of organs and tissues including human digestive tract organs, respiratory tract organs, and urogenital organs, in surgery for forming a channel, and in surgery for closing a cut, and are particularly suitable for staples where organs and tissues are exposed and difficult to operate, so as to reduce operative time and improve quality of surgery.

As described in US Patent Publication No. 20070194082 and 20090255978, various well-known staple shaping mechanisms of surgical staplers each mainly include: a staple cartridge and a staple anvil. Staple drivers, staples, and a cutter are mounted in the staple cartridge, where the cutter may be mounted as needed. A tissue contacting surface of the staple anvil is provided with staple pockets corresponding to the position of the staples in the staple cartridge. The staples and the staple pockets in the staple shaping mechanism of the surgical stapler have the following effects during the use of the surgical stapler. After the tissue to be stapled is clamped between the staple anvil and the staple cartridge, the staple drivers pushes the staples out of the staple cartridge, so that staple tips penetrate the clamped tissue to be stapled, and engage the staple pocket on the staple anvil, so as to bend the U-shaped staples into a B-shaped, thereby achieving the surgical purpose of stapling the tissue.

As described in US Patent Publication No. 20070194082 and 20080061109, in various well-known surgical staplers, as shown in FIG. 1 of the present invention, a staple pocket 2 on the tissue contacting surface of an anvil 1 comprises a side surface 3 and a bottom surface 4 which are formed through inward recessing on the surface of the anvil 1. Intersection lines between the side surface 3 and the bottom surface 4 of the staple pocket 2 form two staple guide lines 5 and 6 of the staple pocket 2. The staple pocket 2 forms perimeter 7 on the surface of the anvil 1. As shown in FIG. 2 of the present invention, a staple 8 in a staple cartridge (not shown) is U-shaped, and comprises a straight back span 9 and two straight staple legs 10 and 11. End portions of the legs 10 and 11 are provided with tips 12 and 13 respectively. As shown in FIG. 3 to FIG. 5 of the present invention, when a staple driver 14 pushes the staple 8 out of the staple cartridge (not shown), the tips 12 and 13 of the U-shaped staple 8 are urged against the staple pocket 2 of the anvil 1, so that the legs 10 and 11 of the U-shaped staple 8 bend along the staple guide lines 5 and 6 of the staple pocket 2, to form a B-shaped staple 15, thereby achieving the surgical purpose of tissue stapling. After the U-shaped staple 8 bends to form the B-shaped staple 15, two rings 16 and 17 are formed, so that a clamping force of the stapled tissue between the legs and the back span is distributed in the two rings 16 and 17, that is, is distributed on a length less than a half of the back span 9, which incurs larger damage to the stapled tissue. Smaller size of the rings 16 and 17 facilitates sealing and bleeding-stopping of the stapled tissue, but makes healing of surrounding tissues slower. Larger size of the rings 16 and 17 facilitates healing of surrounding tissues, but results in poor sealing of the stapled tissue and a poor hemostatic effect. Generally speaking, the edge of the stapled tissue is required to facilitate sealing and bleeding-stopping, and the inner side of the edge of the stapled tissue is required to facilitate healing of the surrounding tissues. In order to achieve the surgical effect, staple cartridges loaded with U-shaped staples having legs of different heights and/or a staple anvil provided with staple pockets in different depths are required to be adopted, the surgical staples and the staple pockets of this kind of surgical stapler increase the difficulty in machining and mounting of the instrument, thereby increasing the cost of the instrument. On the other hand, when the staple 8 bends to form a B-shaped closed staple 15, the tips 12 and 13 of the staple 15 converge at a midpoint of the back span 9, so that in order to achieve the surgical purpose of tissue stapling, for tissues to be stapled and varying in clamping thickness, U-shaped staples having legs of different heights are required to be used. Therefore, during surgery the thickness of the tissue to be stapled is required to be determined first, and then the staple cartridge of U-shaped staples having legs of a different height is used. The specifications of the staple cartridge loaded with U-shaped staples having legs of different heights are limited, and normally for each difference of 0.5 mm in the tissue clamping thickness, there is a specification, so that the surgical staple and the staple pocket of this kind cannot meet surgical requirements of tissues varying in thicknesses to be stapled, thereby deteriorating the surgical effect, increasing the difficulty in surgery, and increasing surgical costs. Therefore, the surgical staple and the staple pocket are required to be improved.

As described in US Patent Publication No. 20090255978: as shown in FIG. 1 of the present invention, a staple pocket 2 on the tissue contacting surface of an anvil 1 comprises a side surface 3 and a bottom surface 4 which are formed through inward recessing on the surface of the anvil 1. Intersection lines between the side surface 3 and the bottom surface 4 of the staple pocket 2 form two staple guide lines 5 and 6 of the staple pocket 2. The staple pocket 2 forms perimeter 7 on the surface of the anvil 1. As shown in FIG. 6 of the present invention, an staple 18 of a surgical stapler in a staple cartridge (not shown) comprises a W-shaped back span 19 and two straight legs 20 and 21. End portions of the legs 20 and 21 are provided with tips 22 and 23 respectively. As shown in FIG. 7 to FIG. 9 of the present invention, two protruding parts 24 and 25 on the W-shaped back span 19 of the staple 18 correspond to positions of two recessed grooves 26 and 27 on the staple pocket 2 of the anvil 1 respectively. When the staple driver 28 pushes the staple 18 out of the staple cartridge (not shown), the tips 22 and 23 of the staple 18 are urged against the staple pocket 2 of the anvil 1, so that the two legs 20 and 21 of the staple 18 bend along staple guide lines 5 and 6 of the staple pocket 2 to form a B-shaped staple 29, thereby achieving the surgical purpose of tissue stapling. Therefore, when tissue to be stapled and having the same clamping thickness are stapled, the surgical requirements of facilitating sealing and bleeding-stopping of the edge of the stapled tissue and facilitating healing of the surrounding tissue of the inner side of the edge of the stapled tissue are met respectively by adopting the staple anvil provided with the staple pocket of the same depth and adopting the staple cartridge loaded with staples having legs of the same height and having the W-shaped back spans 19 having the protruding parts 24 and 25 of different heights. However, when the staple 18 bends to form the staple 29 in the shape of a complete B, the tips 22 and 23 of the staple 29 also converge at a midpoint of the W-shaped back span 19, so that a clamping force of the stapled tissue between the legs 20 and 21 and the back span 19 is distributed in the two rings of the B-shaped staple 29, that is, is distributed on a length less than a half of the back span 19, which incurs large damage to the stapled tissue. Further, in order to achieve the surgical purpose of tissue stapling, for tissue varying in clamping thickness to be stapled, staples having legs of different heights are required to be used. Therefore, during surgery the thickness of the tissue to be stapled is required to be determined first, and then the staple cartridge with staples having legs of a different height is used. The specifications of the staple cartridge loaded with staples having legs of different heights are limited, and normally for each difference of 0.5 mm in the tissue clamping thickness, there is a specification, so that the surgical staple the staple pocket of this kind cannot meet surgical requirements of tissues varying in thicknesses to be stapled, thereby deteriorating the surgical effect, increasing the difficulty in surgery, and increasing surgical costs. Therefore, the surgical staple and the staple pocket are required to be improved.

As described in US Patent Publication No. 20110087276: as shown in FIG. 2 of the present invention, an staple 8 in a staple cartridge (not shown) is U-shaped, and comprises a straight back span 9 and two straight legs 10 and 11. End portions of the legs 10 and 11 are provided with tips 12 and 13 respectively. As shown in FIG. 10 of the present invention, the tissue contacting surface of a staple anvil 30 is provided with two separate staple pockets 31 and 32, which respectively comprise side surfaces 33 and 34 and bottom surfaces 35 and 36 formed through inward recessing on the surface of the staple anvil 30. Intersection lines between the side surface 33 and the bottom surface 35 form two staple guide lines 37 and 38 of the staple pocket 31. Intersection lines between the side surface 34 and the bottom surface 36 form two staple guide lines 39 and 40 of the staple pocket 32. The two staple pockets 31 and 32 form perimeters 41 and 42 on the surface of the staple anvil 30 respectively. As shown in FIG. 11 to FIG. 13 of the present invention, when a staple driver 43 pushes the staple 8 out of the staple cartridge (not shown), the tips 12 and 13 of the staple 8 are urged against the staple pockets 31 and 32 of the staple anvil 30 respectively, so that the two legs 10 and 11 of the staple 8 bend along the staple guide lines 37 and 38 of the staple pocket 31 and the staple guide lines 39 and 40 of the staple pocket 32 respectively, to form a spiral staple 44, thereby achieving the surgical purpose of tissue stapling. When the two legs 10 and 11 of the staple 8 bend to form the spiral staple 44, the tips 12 and 13 of the staple 8 do not converge at a midpoint of the back span 9, so that tissues varying in clamping thickness to be stapled do not require staples having legs of different heights to be used, that is, the staple cartridge loaded with the staples having the legs being the same in height is applicable to stapling tissues varying in clamping thickness. However, a large spacing 47 is formed between the spiral staple 44 and the crossing legs 45 and 46, which is likely to incur leakage and bleeding at the edge of the stapled tissue, so that in order to facilitate sealing and bleeding-stopping of the edge of the stapled tissue, an embodiment of the surgical stapler using the spirally shaped staples in the US Patent Publication No. 20110087276 uses more rows of staples than the surgical stapler using B-shaped staples, which increases the volume of the surgical stapler and the stapling width of the stapled tissue, thereby not only shrinking the application scope of the surgery using the surgical stapler but also increasing the cost of the surgical stapler. Therefore, the surgical staple and the staple pocket are required to be improved.

It can be obviously seen from the above that, a large number of varieties of surgical staplers have been designed, and the development work of the staples and the staple pockets for new surgical staplers continues, so as to further improve the surgical staplers that are annually extensively used around the world, aiming at achieving the surgical purpose of reliable tissue stapling, making the use convenient, and reducing the costs.

SUMMARY OF THE PRESENT INVENTION

An objective of the present invention is to provide surgical staple and staple pocket for forming kidney-shaped staple, so that a back span and two legs of an staple form an M-shaped staple, and a staple pocket comprises a side surface, a bottom surface, and an oblique ridge that are formed after the staple pocket is inward recessed on the tissue contacting surface of a staple anvil. Therefore, when tissue varying in thickness is stapled by using staples of the same height, each staple driver pushes the M-shaped staple out of the staple cartridge, and urges tips of the M-shaped staple against the staple pocket of the staple anvil, so that the two legs of the M-shaped staple bend along staple guide lines of the staple pocket respectively, so as to bend the M-shaped staple to form a kidney-shaped staple, thereby not only achieving the surgical effect of facilitating sealing and bleeding-stopping of the edge of the stapled tissue and facilitating the healing of the surrounding tissue of the inner side of the edge of the stapled tissue, but also making the use of the surgical stapler convenient and reducing the costs.

Another objective of the present invention is to provide surgical staple and staple pocket for forming kidney-shaped staple, so that multiple staple pockets are staggered-arranged on two or more rings or in two or more rows on the tissue contacting surface of a staple anvil, and positions of M-shaped staples arranged in a staple cartridge correspond to positions of the staple pockets arranged on the surface of the staple anvil. The degree in which a middle portion of a back span of the M-shaped staple arranged on an inner ring or on a near side of the cutter slot protrudes towards tips of two legs may be greater than the degree in which the middle portion of the back span of the M-shaped staple arranged on an outer ring or on a far side of the cutter slot protrudes towards the tips of the two legs. Therefore, when staples of the same height are used to staple tissue varying in thickness, not only the surgical effect of facilitating sealing and bleeding-stopping of the edge of the stapled tissue is achieved, but also the surgical effect of facilitating the healing of the surrounding tissue of the inner side of the edge of the stapled tissue is achieved.

Currently, the well-known surgical staples are located in the staple cartridge, the staple comprises a back span and two legs, and end portions of the two legs are provided with tips respectively; the well-known staple pocket comprises a side surface and a bottom surface that are formed after inward recessing on the tissue contacting surface of the staple anvil, and the staple pockets forms perimeters on the surface of the staple anvil. Staple drivers push the staples out of the staple cartridge, and urge the tips of the staples against the staple pockets of the staple anvil, so as to bend the legs of the staples.

The present invention is achieved through the following technical solutions.

In surgical staple and staple pocket for forming kidney-shaped staple according to the present invention, the staple pocket comprises a side surface, a bottom surface, and an oblique ridge that are formed after the staple pocket is inward recessed on the tissue contacting surface of a staple anvil, a ridge line of an oblique ridge and a long axis of the staple pocket intersect and form an acute angle, a ridge top of the oblique ridge is inward recessed towards the bottom surface, the oblique ridge divides the bottom surface into two parts, and intersection lines between the side surface and the oblique ridge of the staple pocket and the bottom surface form staple guide lines of the staple pocket. The staples are located in a staple cartridge. The staple comprises a back span and two legs, end portions of the two legs are provided with tips respectively, and a middle portion of the back span protrudes towards the tips of the two legs, so that the back span and the two legs of the staple form an M-shaped staple. The axis of the back span may comprise several curve segments, may also comprise several straight line segments, and may also comprise curve segment and straight line segment, so that the back span and the two legs of the staple form the M-shaped staple. The section of the back span and legs of the staple may be round or not, and may also be polygonal. The pointed ends of two tips of a staple may be located on each outer side of the staple, and may also be located on each inner side of the staple.

When a staple driver pushes the M-shaped staple out of the staple cartridge, the staple driver urges the tips of the two legs of the M-shaped staple against the staple pocket of the staple anvil, so that the two legs of the M-shaped staple bend along the staple guide lines of the staple pocket respectively, and meanwhile a portion, in the middle of the back span and protruding towards the tips of the two legs, moves towards a portion, inward recessed towards the bottom surface, of the ridge top of the oblique ridge on the staple pocket of the staple anvil, so as to bend the M-shaped staple to form a kidney-shaped staple.

When the M-shaped staple is bent to form a kidney-shaped staple, the two legs of the M-shaped staple cross each other and bend, so that the two tips deviate from the middle portion of the back span. Therefore, tissues to be stapled and varying in clamping thickness do not require staples having legs of different heights to be used, that is, the staple cartridge loaded with the staples having the legs being the same in height is applicable to stapling tissue varying in clamping thickness. After the M-shaped staple is bent to form the kidney-shaped staple, the portion, in the middle of the back span of the M-shaped staple and protruding towards the tips of the two legs, protrudes into the crossing legs of the kidney-shaped staple, so that a spacing formed between the legs and the back span is narrow and long, the clamping force of the stapled tissue between the legs and the back span is distributed on the whole length of the back span, so as to achieve not only the surgical effect facilitating sealing and bleeding-stopping of the stapled tissue but also the surgical effect of facilitating healing of the surrounding tissue of the inner side of the edge of the stapled tissue, and achieve the use effect of making the use of the surgical stapler convenient and reducing the costs.

The staple anvil of the present invention may be circular. Multiple staple pockets are staggered-arranged on two or more rings on the surface of the circular staple anvil. The positions of the M-shaped staples arranged in the staple cartridge correspond to the positions of the staple pockets arranged on the tissue contacting surface of the circular staple anvil. The degree in which the middle portion of the back span of the M-shaped staple arranged on an inner ring protrudes towards the tips of the two legs may be greater than the degree in which the middle portion of the back span of the M-shaped staple arranged on an outer ring protrudes towards the tips of the two legs, and may also be the same as the degree in which the middle portion of the back span of the M-shaped staple arranged on the outer ring protrudes towards the tips of the two legs. Extension lines of ridge lines of oblique ridges of two adjacent staple pockets on two adjacent rings may intersect.

The staple anvil of the present invention may be linear, and may specifically be in the shape of a straight line or in the shape of a curve. Multiple staple pockets are staggered-arranged in two or more rows on the tissue contacting surface of the linear staple anvil. Extension lines of ridge lines of oblique ridges of two adjacent staple pockets in two adjacent rows may intersect. The linear staple anvil may be provided with a cutter slot. Multiple staple pockets are arranged on two sides of the cutter slot of the linear staple anvil. The positions of the M-shaped staples arranged in the staple cartridge correspond to the positions of the staple pockets arranged on the surface of the linear staple anvil. The degree in which the middle portion of the back span of the M-shaped staple arranged on a near side of the cutter slot of the linear staple anvil protrudes towards the tips of the two legs may be greater than the degree in which the middle portion of the back span of the M-shaped staple arranged on a far side of the cutter slot protrudes towards the tips of the two legs, and may also be the same as the degree in which the middle portion of the back span of the M-shaped staple arranged on the far side of the cutter slot protrudes towards the tips of the two legs.

Multiple staple pockets are staggered-arranged on two or more rings or in two or more rows on the tissue contacting surface of the staple anvil, and the positions of the M-shaped staples arranged in the staple cartridge correspond to the positions of the staple pockets on the surface of the staple anvil, so that after the M-shaped staples are bent to form the kidney-shaped staples, the kidney-shaped staples of two adjacent rows collectively block gaps between the staples, thereby achieving the surgical effect of facilitating sealing and bleeding-stopping of the stapled tissue. Further, the extension lines of the ridge lines of the oblique ridges of two adjacent staple pockets on two adjacent rings or in two adjacent rows intersect, so that after the M-shaped staples are bent to form the kidney-shaped staples, the positions of the tips of the legs of two adjacent kidney-shaped staples on the two adjacent ring or in the two adjacent rows are staggered relative to each other, so as to achieve not only the surgical effect of facilitating sealing and bleeding-stopping of the stapled tissue but also the surgical effect of enhancing the strength at the stapled tissue. If the degree in which the middle portion of the back span of the M-shaped staple arranged on the inner ring or on the near side of the cutter slot protrudes towards the tips of the two legs is greater than the degree in which the middle portion of the back span of the M-shaped staple arranged on the outer ring or on the far side of the cutter slot protrudes towards the tips of the two legs, when staples having legs of the same height are used to staple tissues varying in thickness, not only the surgical effect of facilitating sealing and bleeding-stopping of the edge of the stapled tissue can be achieved, but also the surgical effect of facilitating the healing of the surrounding tissue of the inner side of the edge of the stapled tissue can be achieved.

The surgical staples and staple pockets for forming kidney-shaped staples in the present invention may be used in combination with surgical staples and staple pockets of another type according to surgical requirements on tissue stapling. For example, one ring or one row adopts the surgical staples and staple pockets for forming kidney-shaped staple in the present invention, and another ring or another row adopts surgical staples and staple pockets of another type.

BRIEF DESCRIPTION OF THE DRAWINGS

FIG. 23 is an outside view of an M-shaped staple having a back span with the axis comprising of a bent line according to an embodiment of the present invention.

FIG. 24 is an outside view showing that a staple driver urges tips of an M-shaped staple of FIG. 23 against a staple pocket of a staple anvil.

FIG. 25 is an outside view showing that an M-shaped staple of FIG. 23 bends on a staple pocket of a staple anvil to form a kidney-shaped staple.

FIG. 26 is an outside view of a kidney-shaped staple of FIG. 25 shaped by bending.

FIG. 27 is an outside view of an M-shaped staple having a back span with the axis comprising of a curve and a bent line according to an embodiment of the present invention.

FIG. 28 is an outside view showing that a staple driver urges tips of an M-shaped staple of FIG. 27 against a staple pocket of a staple anvil.

FIG. 29 is an outside view showing that an M-shaped staple of FIG. 27 bends on a staple pocket of a staple anvil to form a kidney-shaped staple.

FIG. 30 is an outside view of a kidney-shaped staple of FIG. 29 shaped by bending.

DETAILED DESCRIPTION OF THE PREFERRED EMBODIMENTS

Preferred embodiments of surgical staple and staple pocket for forming kidney-shaped staple according to the present invention are described below through examples with reference to the accompanying drawings. The scope of the present invention is specified by the claims. It should be known that some or all of the accompanying drawings are schematic drawings for illustrating the preferred embodiments of the present invention, and do not illustrate the real size of what is shown. By referring to the detailed descriptions of the preferred embodiments, the above and other objectives and advantages of the present invention may be better understood.

The processes of various surgical staples and staple pockets for forming kidney-shaped staples according to embodiments of the present invention are described below with reference to FIG. 14 to FIG. 40, so as to illustrate effects of the kidney-shaped surgical staples and the staple pockets.

Figure 1:
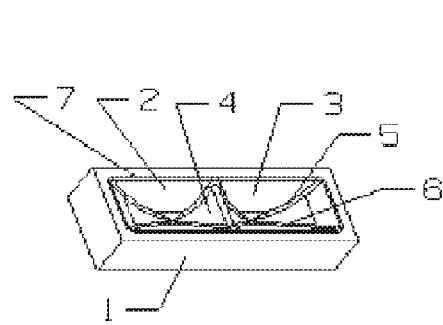
FIG. 1 is an outside view of a well-known staple pocket.
Figure 2:
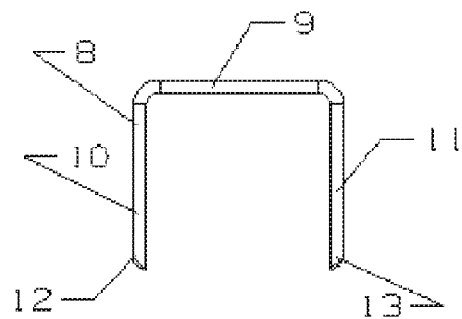
FIG. 2 is an outside view of a well-known U-shaped staple.
Figure 3:
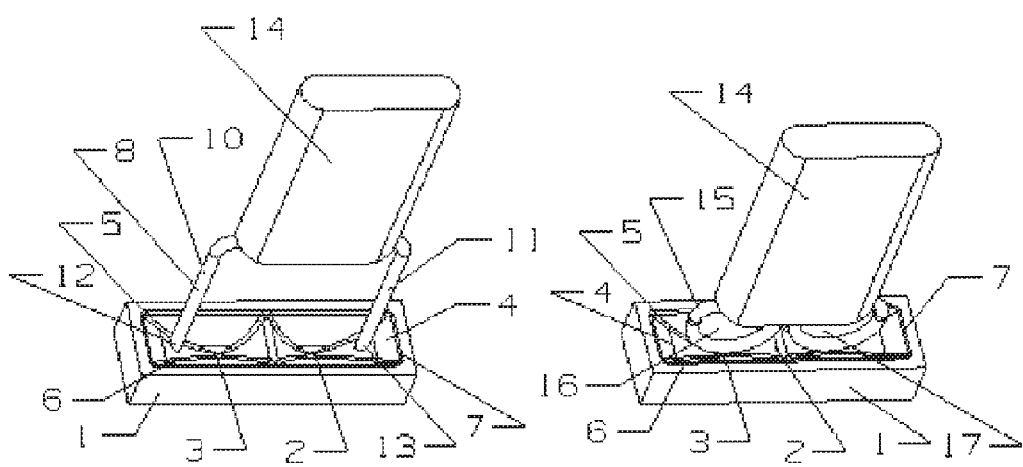
FIG. 3 is an outside view showing that a staple driver urges tips of a well-known U-shaped staple against a staple pocket of a staple anvil.
Figure 4:
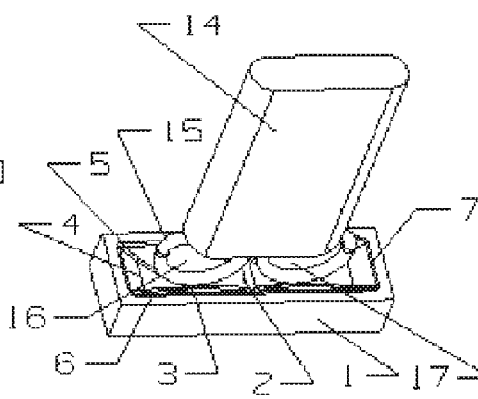
FIG. 4 is an outside view showing that a well-known U-shaped staple bends on a staple pocket of a staple anvil to form a B-shaped staple.
Figure 5:
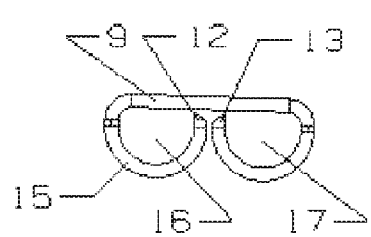
FIG. 5 is an outside view of a well-known B-shaped staple that is shaped by bending.
Figure 6:
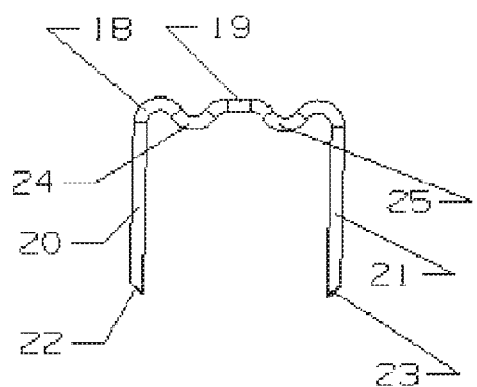
FIG. 6 is an outside view of a well-known staple with a back span being W-shaped.
Figure 9:
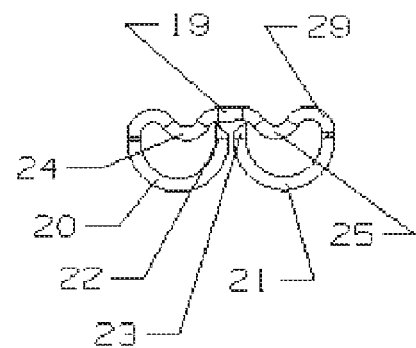
FIG. 9 is an outside view of a well-known staple, with a back span being W-shaped, shaped by bending.
Figure 7:
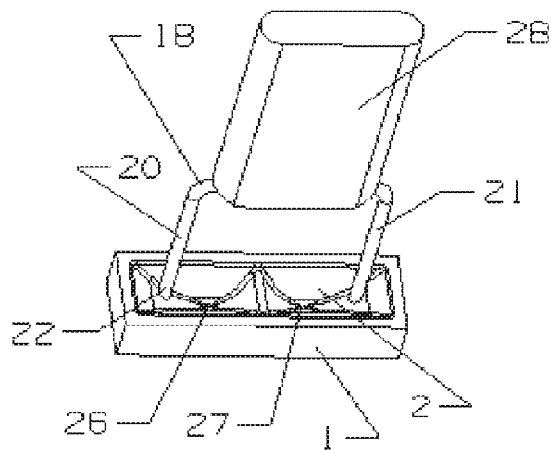
FIG. 7 is an outside view showing that a staple driver urges tips of a well-known staple, with a back span being W-shaped, against a staple pocket of a staple anvil.
Figure 8:
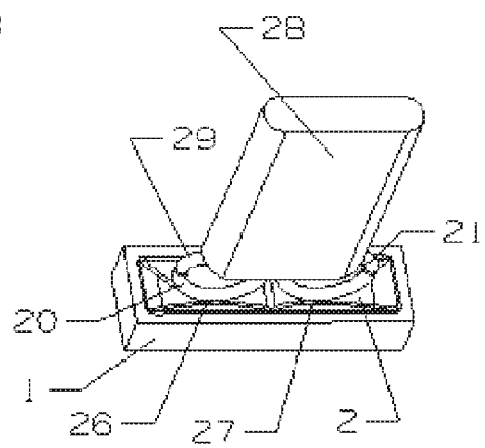
FIG. 8 is an outside view showing that a well-known staple, with a back span being W-shaped, is shaped on a staple pocket of a staple anvil by bending.
Figure 10:
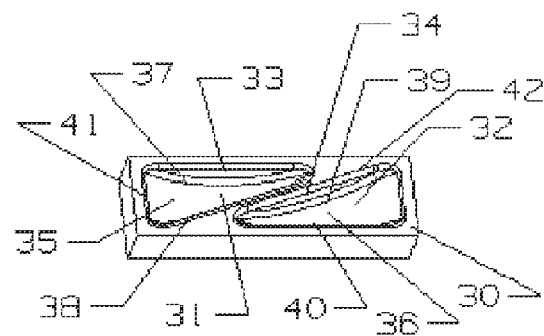
FIG. 10 is an outside view of well-known bias-arranged staple pockets.
Figure 13:
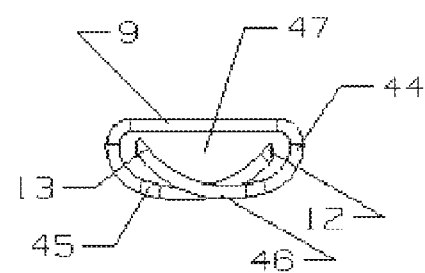
FIG. 13 is an outside view of a well-known spiral staple that is shaped by bending.
Figure 11:
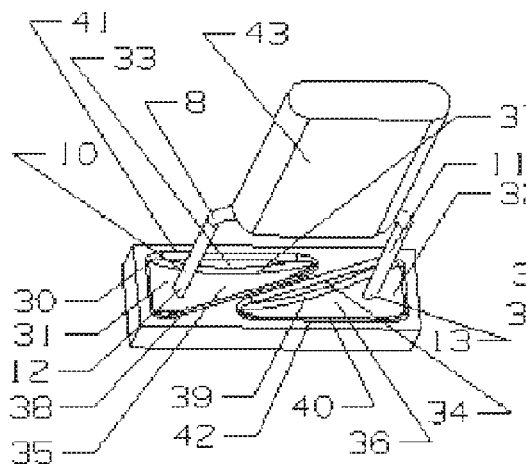
FIG. 11 is an outside view showing that a staple driver urges tips of a well-known U-shaped staple against bias-arranged staple pockets of a staple anvil.
Figure 12:
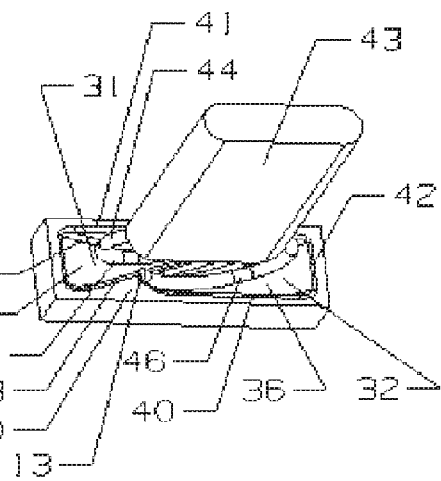
FIG. 12 is an outside view showing that a well-known U-shaped staple bends on bias-arranged staple pockets of a staple anvil to form a spiral staple by bending.
Figure 14:
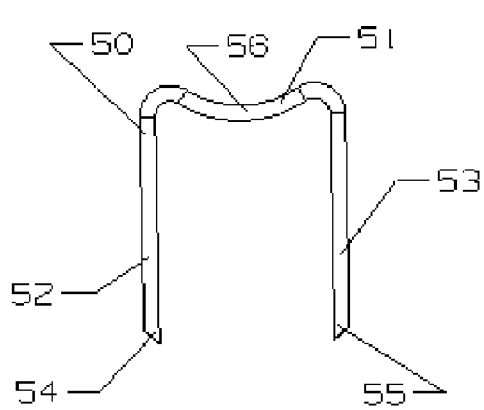
FIG. 14 is an outside view of an M-shaped staple having a back span with the axis comprising of a curve according to an embodiment of the present invention.

As shown in FIG. 14, an staple 50 arranged in a staple cartridge (not shown) comprises a back span 51 and two legs 52 and 53. End portions of the two legs 52 and 53 are provided with tips 54 and 55 respectively. Pointed ends of the tips 54 and 55 of the staple 50 are located on an inner side of the staple 50. A middle portion 56 of the back span 51 protrudes towards the tips 54 and 55 of the two legs 52 and 53, and the axis of the back span 51 comprises several curve segments, so that the back span 51 and the two legs 52 and 53 of the staple 50 form an M-shaped staple 50.

Figure 15:
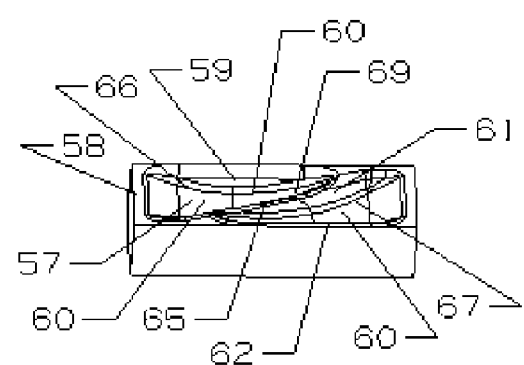
FIG. 15 is an outside view a staple pocket for kidney-shaping according to the present invention.

A staple pocket 57 shown in FIG. 15 comprises a side surface 59, a bottom surface 60, and an oblique ridge 61 that are formed after the staple pocket 57 is inward recessed on a tissue contacting surface of a staple anvil 58. The staple pocket 57 forms perimeter 62 on the surface of the staple anvil 58. A ridge line of the oblique ridge 61 and a long axis of the staple pocket 57 intersect and form an acute angle. A ridge top 65 of the oblique ridge 61 is inward recessed towards the bottom surface 60. The oblique ridge 61 divides the bottom surface 60 into two parts. Intersection lines between the side surface 59 and the oblique ridge 61 of the staple pocket 57 and the bottom surface 60 form staple guide lines 66 and 67 of the staple pocket 57 respectively.

Figure 16:
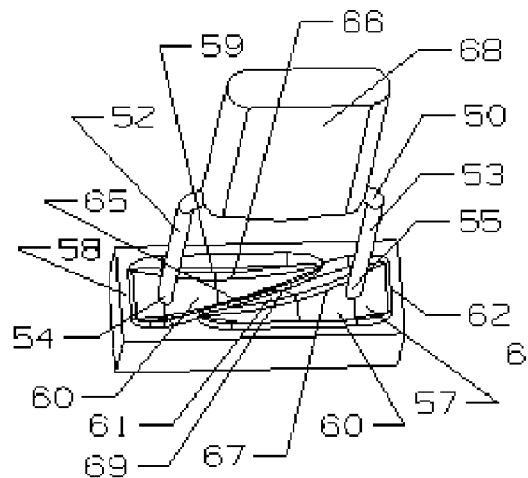
FIG. 16 is an outside view showing that a staple driver urges tips of an M-shaped staple against a staple pocket of a staple anvil.
Figure 17:
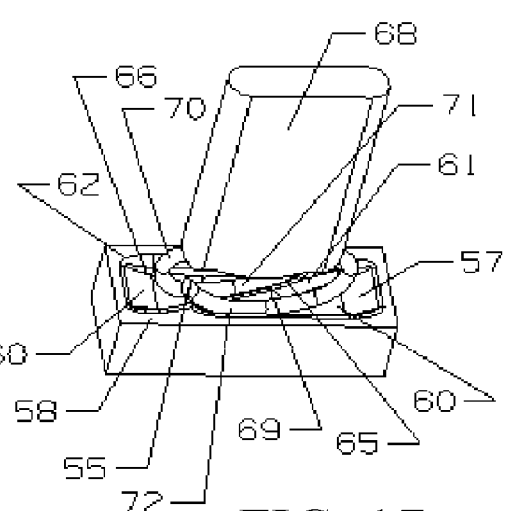
FIG. 17 is an outside view showing that an M-shaped staple bends on a staple pocket of a staple anvil to form a kidney-shaped staple.
Figure 18:
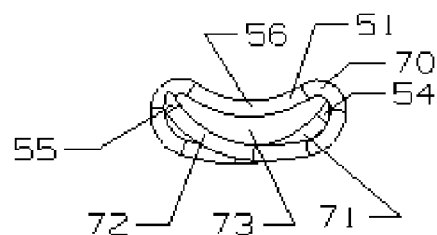
FIG. 18 is an outside view of a kidney-shaped staple shaped by bending.

As shown in FIG. 16 to FIG. 18, when a staple driver 68 pushes the M-shaped staple 50 out of a staple cartridge (not shown), the staple driver 68 urges the tips 54 and 55 of the two legs 52 and 53 of the M-shaped staple 50 against the staple pocket 57 of the staple anvil 58, so that the two legs 52 and 53 of the M-shaped staple 50 bend along the staple guide lines 66 and 67 of the staple pocket 57 respectively, and meanwhile the protruding portion 56 in the middle of the back span 51 moves towards an inward recessed portion 69 of the ridge top 65 of the oblique ridge 61 on the staple pocket 57 of the staple anvil 58, so as to bend the M-shaped staple 50 to form a kidney-shaped staple 70.

Figures 19, 20:
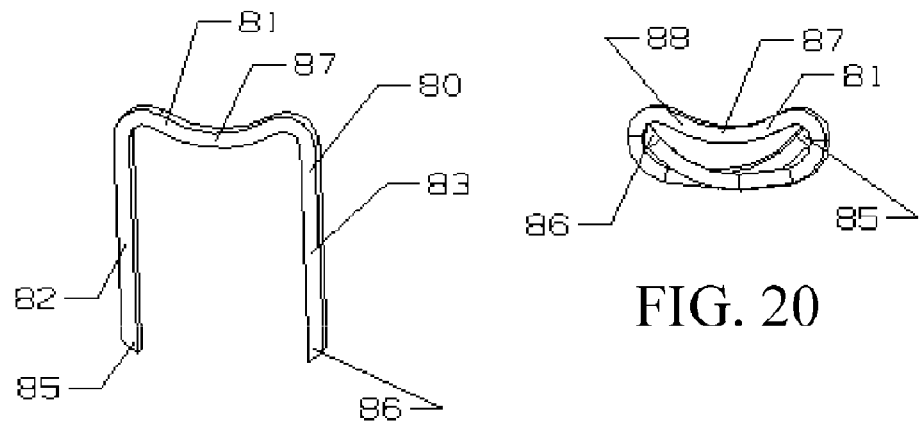
FIG. 19 is an outside view of an M-shaped staple with the section being square according to an embodiment of the present invention.
FIG. 20 is an outside view showing that a staple driver urges tips of an M-shaped staple of FIG. 19 against a staple pocket of a staple anvil.
Figures 21, 22:
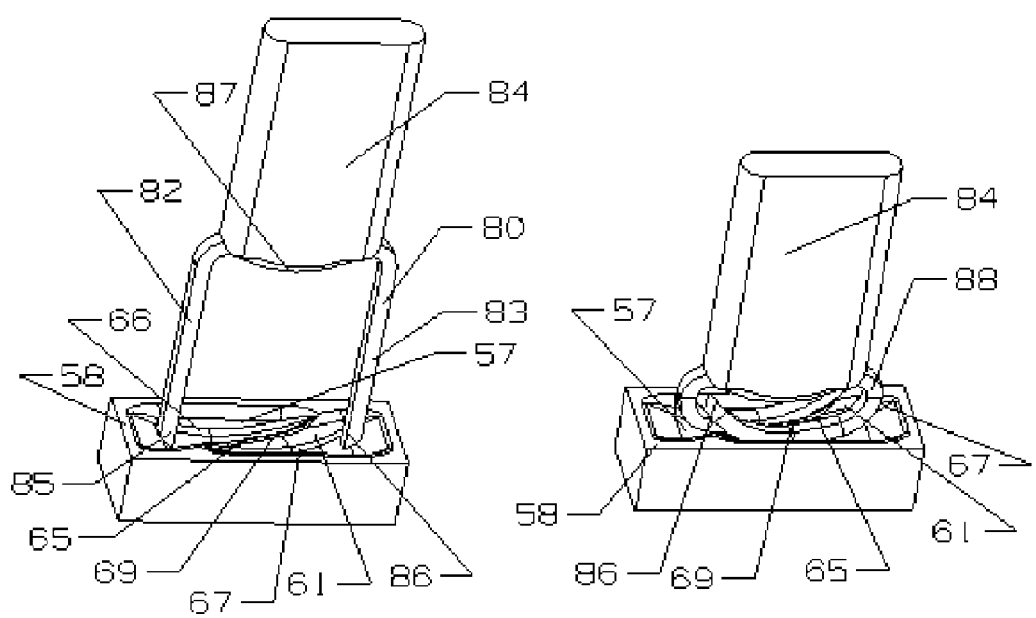
FIG. 21 is an outside view showing that an M-shaped staple of FIG. 19 bends on a staple pocket of a staple anvil to form a kidney-shaped staple.
FIG. 22 is an outside view of a kidney-shaped staple of FIG. 21 shaped by bending.
Figure 31:
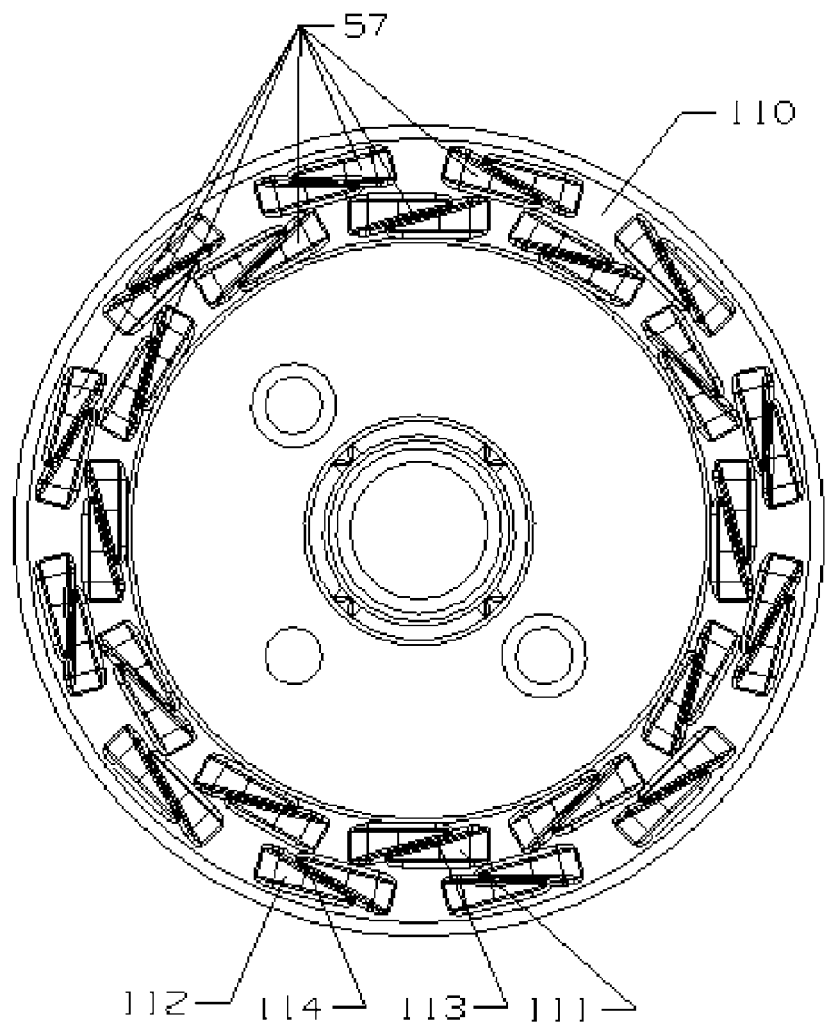
FIG. 31 is an outside view of a circular staple anvil according to an embodiment of the present invention.
Figure 32:
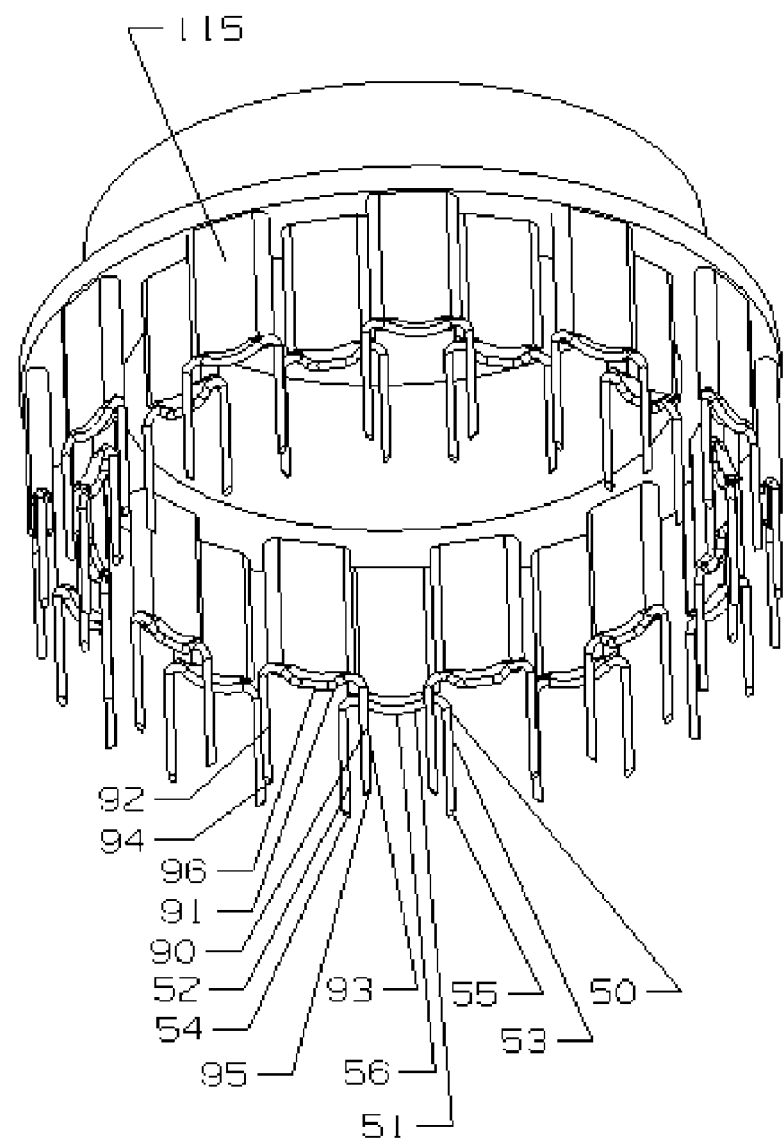
FIG. 32 is an outside view of a staple pushing ring.
Figure 33:
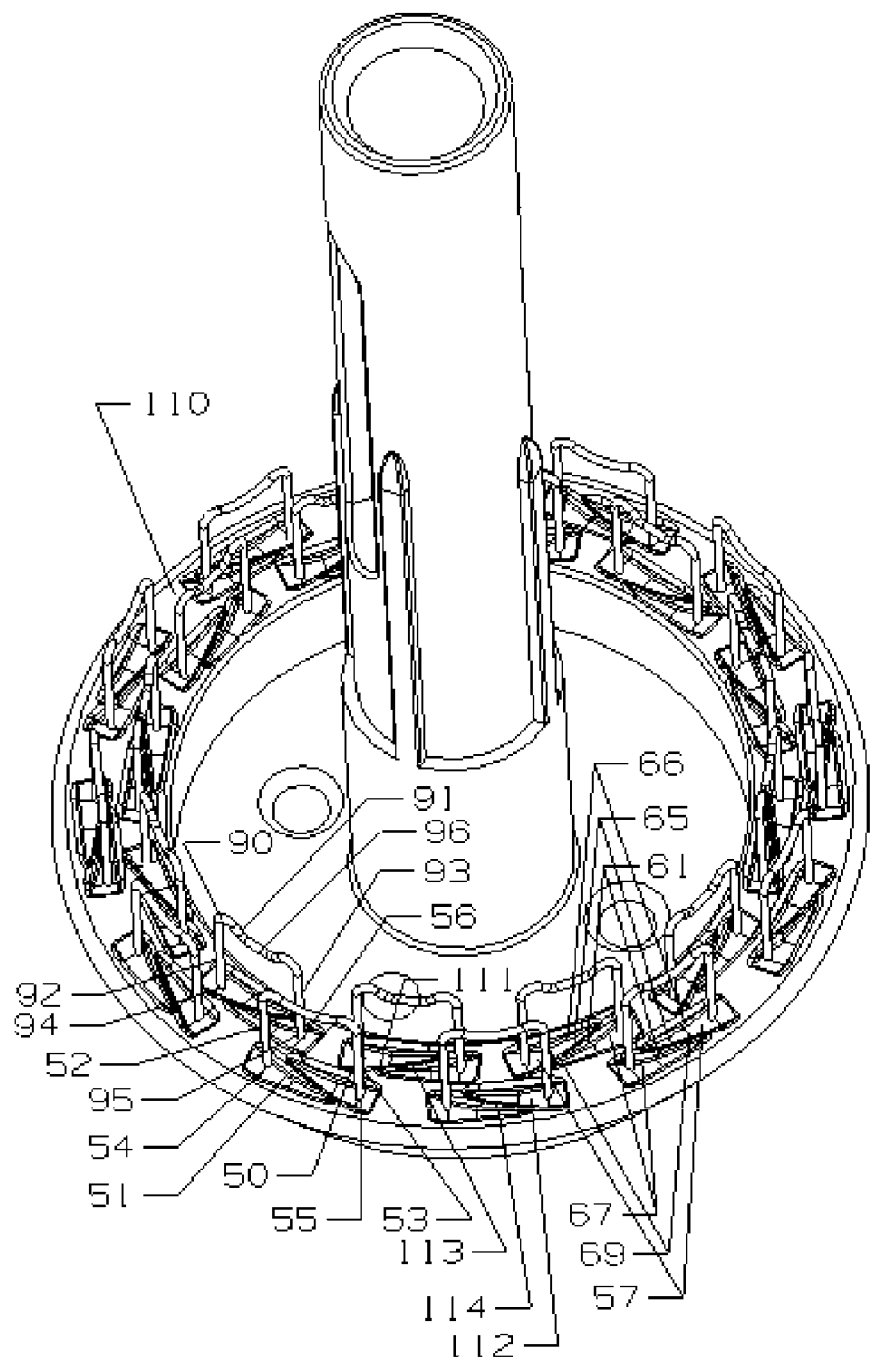
FIG. 33 is an outside view showing that a staple driver urges tips of an M-shaped staple against a staple pocket of a circular staple anvil (the staple pushing ring is removed).
Figure 34:
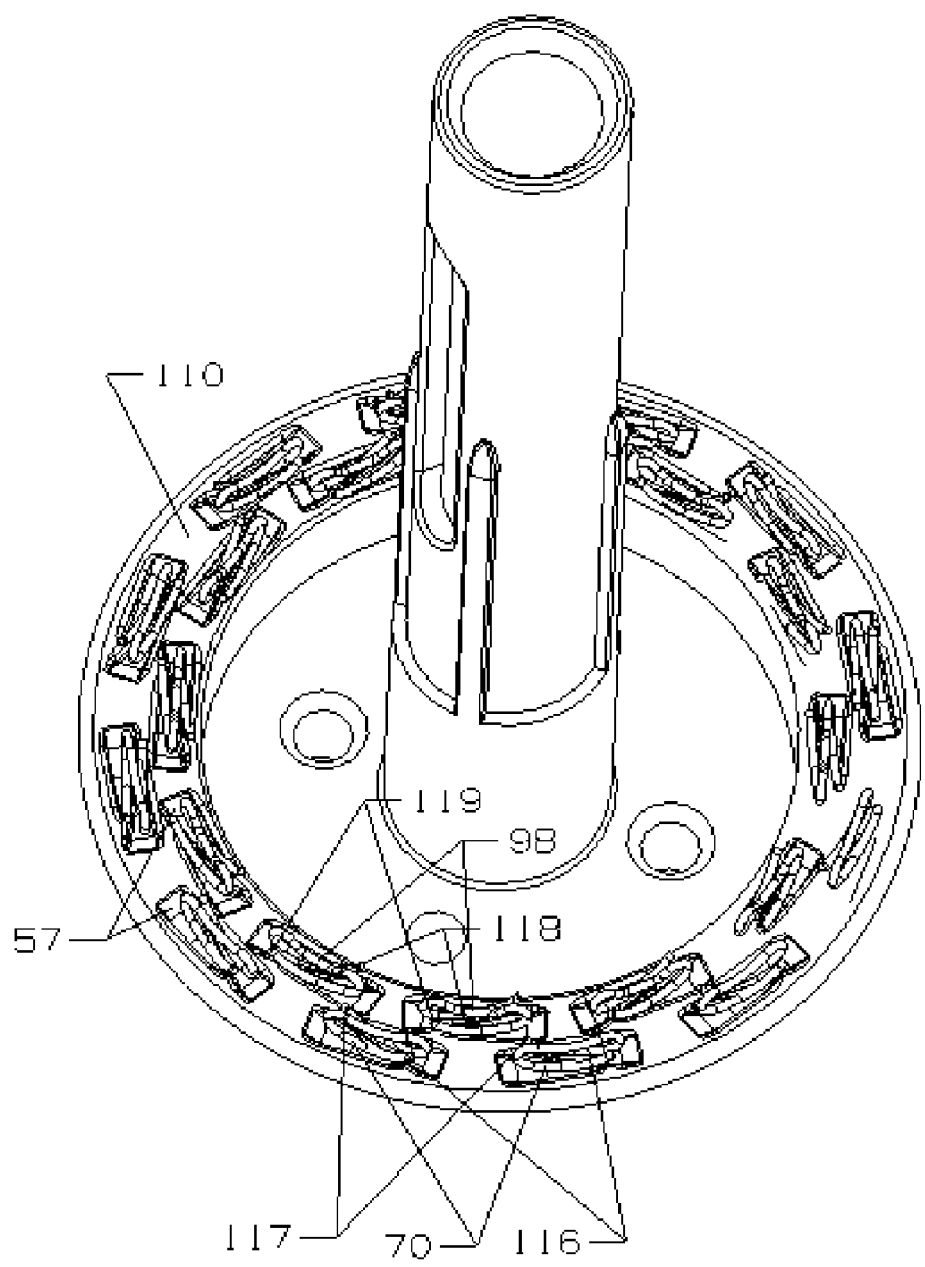
FIG. 34 is an outside view showing that an M-shaped staple bends on a staple pocket of a circular staple anvil to form a kidney-shaped staple.
Figure 35:
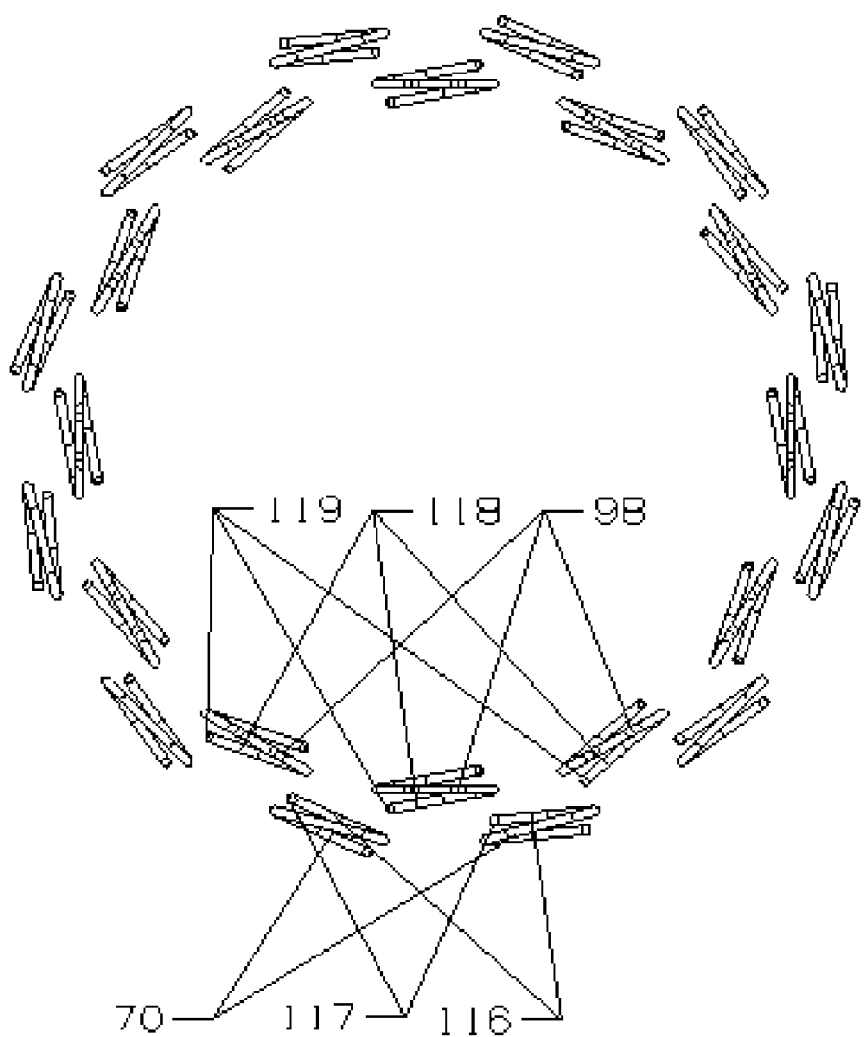
FIG. 35 is an outside view of a kidney-shaped staple shaped by bending on a staple pocket of a circular staple anvil.
Figure 36:
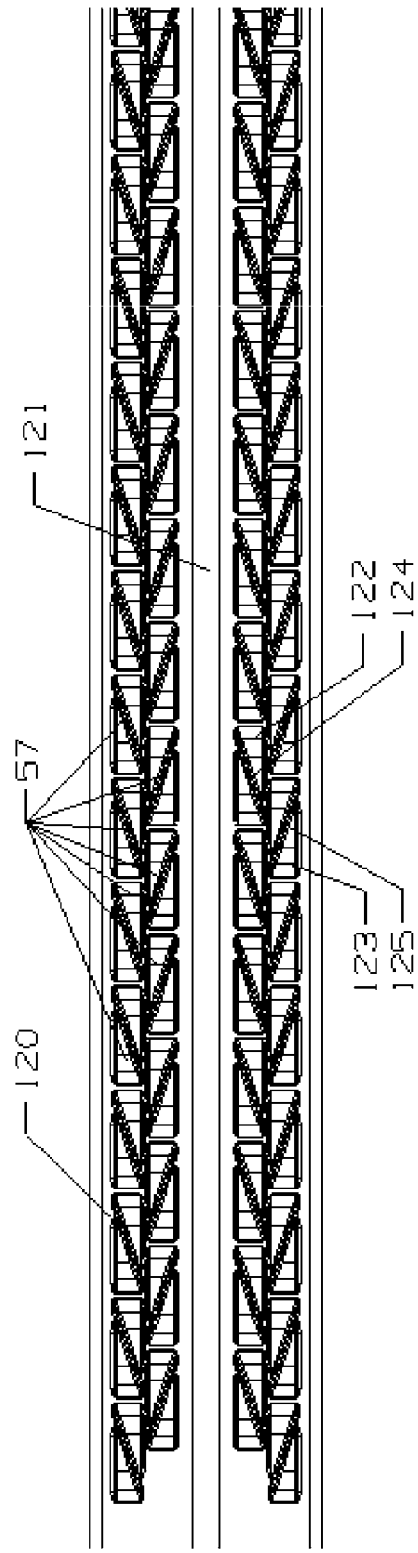
FIG. 36 is an outside view of a linear staple anvil according to an embodiment of the present invention.
Figure 37:
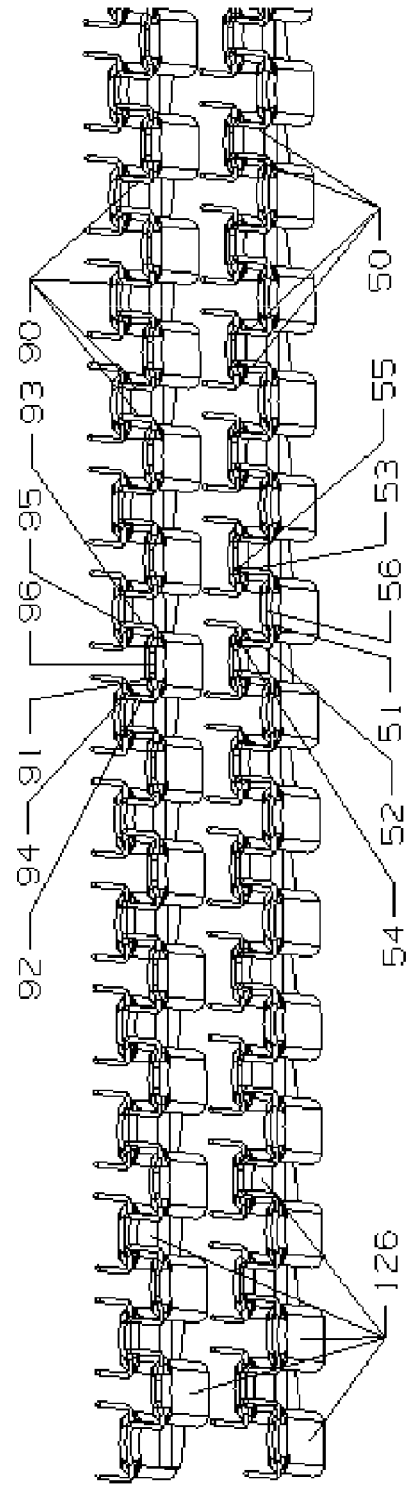
FIG. 37 is an outside view of a staple driver and an M-shaped staple.
Figure 38:
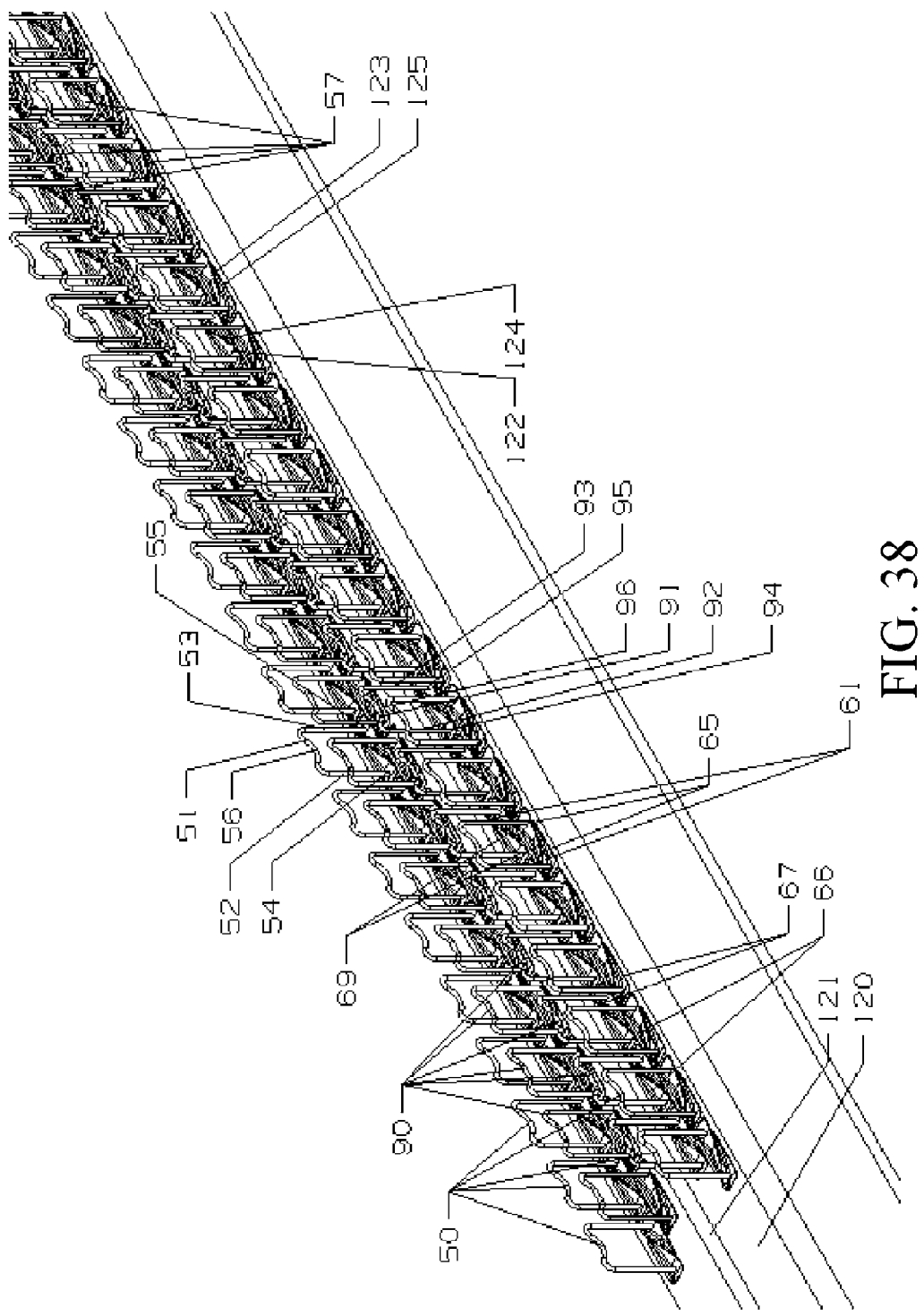
FIG. 38 is an outside view showing that a staple driver urges tips of an M-shaped staple against a staple pocket of a linear staple anvil (the staple pushing ring is removed).
Figure 39:
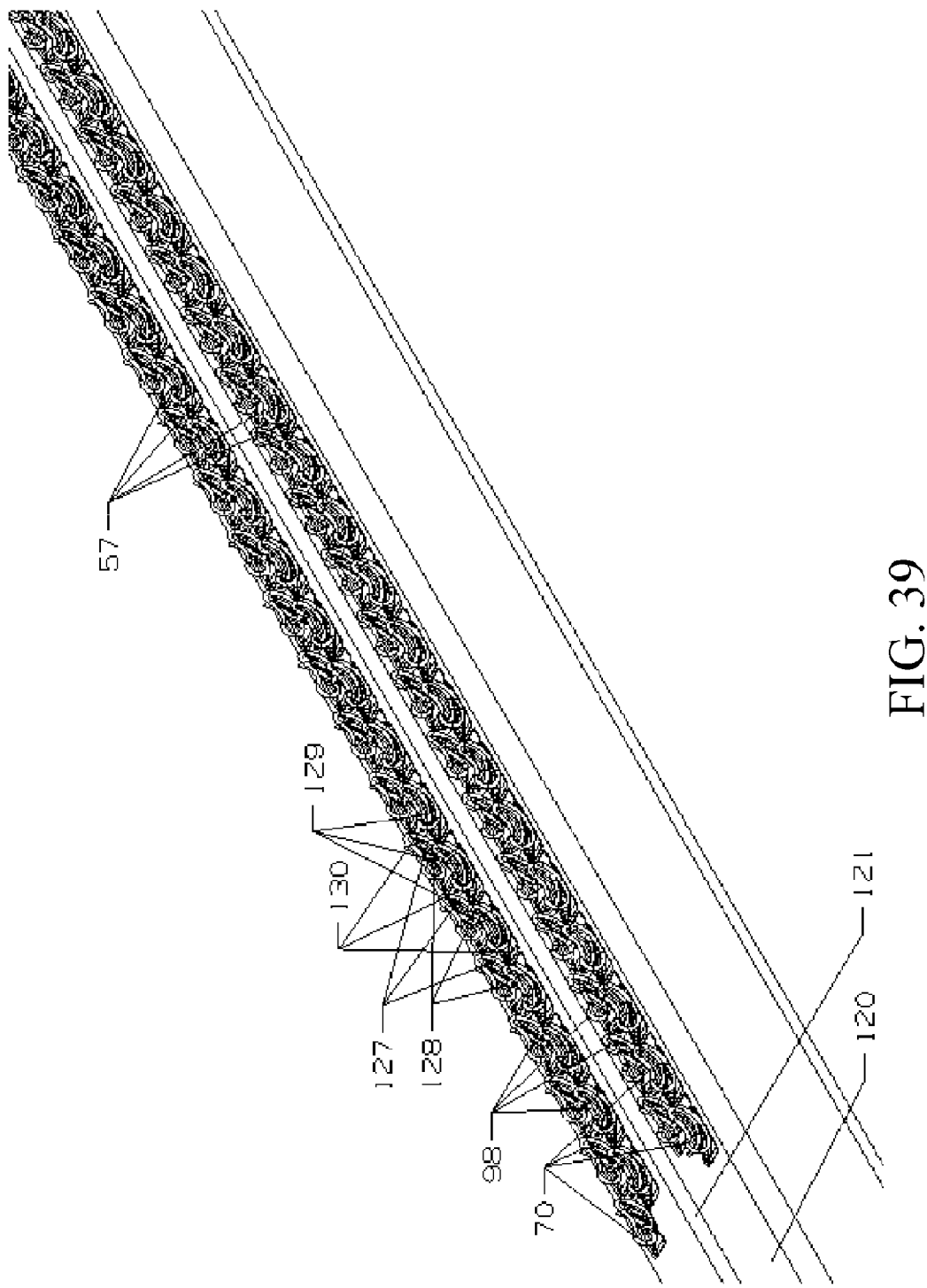
FIG. 39 is an outside view showing that an M-shaped staple bends on a staple pocket of a linear staple anvil to form a kidney-shaped staple.
Figure 40:
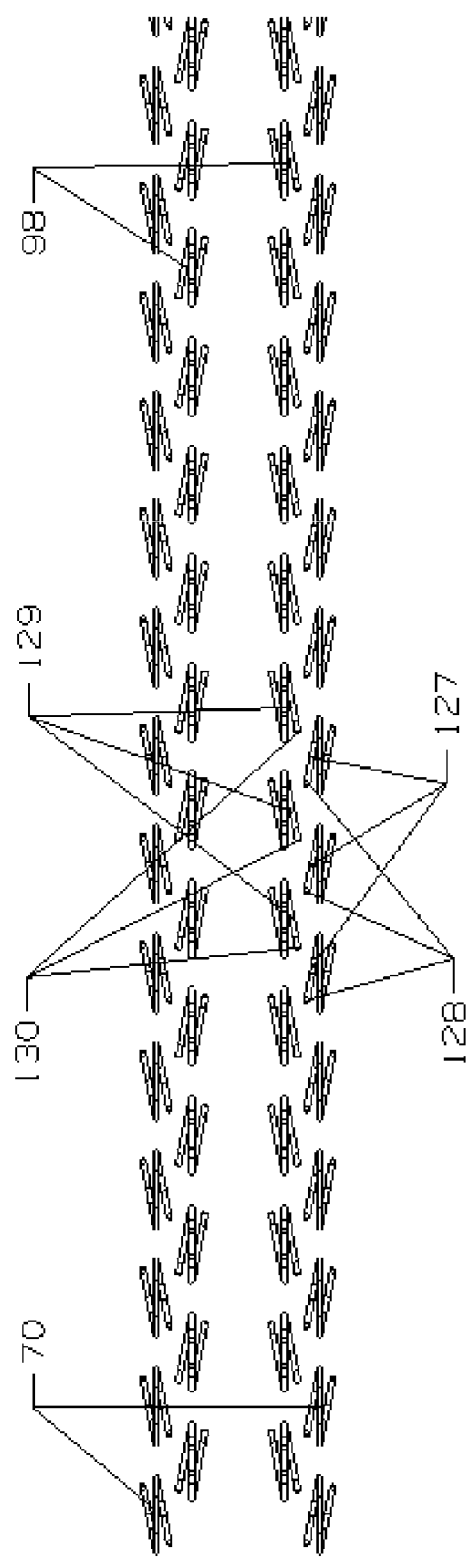
FIG. 40 is an outside view of a kidney-shaped staple shaped by bending on a staple pocket of a linear staple anvil.

The section of the back span and legs of the M-shaped staple may be round as shown in the forgoing drawing, and may be of other shapes. The section of a back span 81 and legs 82 and 83 of an M-shaped staple 80 shown in FIG. 19 is square. As shown in FIG. 20 to FIG. 22, when a staple driver 84 pushes the M-shaped staple 80 out of a staple cartridge (not shown), the staple driver 84 urges tips 85 and 86 of the two legs 82 and 83 of the M-shaped staple 80 against the staple pocket 57 of the staple anvil 58, so that the two legs 82 and 83 of the M-shaped staple 80 bend along the staple guide lines 66 and 67 of the staple pocket 57 respectively, and meanwhile a protruding portion 87 in the middle of the back span 81 moves towards the inward recessed portion 69 of the ridge top 65 of the oblique ridge 61 on the staple pocket 57 of the staple anvil 58, so as to bend the M-shaped staple 80 to form a kidney-shaped staple 88.

As shown in FIG. 23, an staple 90 arranged in a staple cartridge (not shown) comprises a back span 91 and two legs 92 and 93. End portions of the two legs 92 and 93 are provided with tips 94 and 95 respectively. A middle portion 96 of the back span 91 protrudes towards the tips 94 and 95 of the two legs 92 and 93, and the axis of the back span 91 comprises several straight line segments, so that the back span 91 and the two legs 92 and 93 of the staple 90 form an M-shaped staple 90.

As shown in FIG. 24 to FIG. 26, when a staple driver 97 pushes the M-shaped staple 90 out of a staple cartridge (not shown), the staple driver 97 urges tips 94 and 95 of the two legs 92 and 93 of the M-shaped staple 90 against the staple pocket 57 of the staple anvil 58, so that the two legs 92 and 93 of the M-shaped staple 90 bend along the staple guide lines 66 and 67 of the staple pocket 57 respectively, and meanwhile a protruding portion 96 in the middle of the back span 91 moves towards the inward recessed portion 69 of the ridge top 65 of the oblique ridge 61 on the staple pocket 57 of the staple anvil 58, so as to bend the M-shaped staple 90 to form a kidney-shaped staple 98.

As shown in FIG. 27, an staple 100 arranged in a staple cartridge (not shown) comprises a back span 101 and two legs 102 and 103. End portions of the two legs 102 and 103 are provided with tips 104 and 105 respectively. A middle portion 106 of the back span 101 protrudes towards the tips 104 and 105 of the two legs 102 and 103, and the axis of the back span 101 comprises curve segment and straight line segment, so that the back span 101 and the two legs 102 and 103 of the staple 100 form an M-shaped staple 100.

As shown in FIG. 28 to FIG. 30, when a staple driver 107 pushes the M-shaped staple 100 out of a staple cartridge (not shown), the staple driver 107 urges tips 104 and 105 of the two legs 102 and 103 of the M-shaped staple 100 against the staple pocket 57 of the staple anvil 58, so that the two legs 102 and 103 of the M-shaped staple 100 bend along the staple guide lines 66 and 67 of the staple pocket 57 respectively, and meanwhile a protruding portion 106 in the middle of the back span 101 moves towards the inward recessed portion 69 of the ridge top 65 of the oblique ridge 61 on the staple pocket 57 of the staple anvil 58, so as to bend the M-shaped staple 100 to form a kidney-shaped staple 108.

As shown in FIG. 14 to FIG. 18, FIG. 23 to FIG. 26, and FIG. 31 to FIG. 35, multiple staple pockets 57 are staggered-arranged on two rings on a tissue contacting surface of a circular anvil 110. M-shaped staples 50 and staples 90 arranged in a staple cartridge (not shown) correspond to positions of the staple pockets 57 arranged on the surface of the circular anvil 110. The M-shaped staple 50 is arranged on an outer ring of the staple cartridge, and the M-shaped staple 90 is arranged on an inner ring of the staple cartridge. The degree in which the middle portion 96 of the back span 91 of the M-shaped staple 90 arranged on the inner ring protrudes towards the tips 94 and 95 of the two legs 92 and 93 is greater than the degree in which the middle portion 56 of the back span 51 of the M-shaped staple 50 arranged on the outer ring protrudes towards the tips 54 and 55 of the two legs 52 and 53. Extension lines of ridge lines of oblique ridges 113 and 114 of two adjacent staple pockets 111 and 112 on two adjacent rings intersect.

When a staple pushing ring 115 pushes the M-shaped staples 50 and 90 out of a staple cartridge (not shown), the staple pushing ring 115 urges the tips 54 and 55 of the two legs 52 and 53 of each M-shaped staple 50 and the tips 94 and 95 of the two legs 92 and 93 of each M-shaped staple 90 against the staple pockets 57 of the circular anvil 110, so that the two legs 52 and 53 of each M-shaped staple 50 and the two legs 92 and 93 of each M-shaped staple 90 bend along the staple guide lines 66 and 67 of the staple pockets 57 respectively, and meanwhile the protruding portion 56 in the middle of the back span 51 of each M-shaped staple 50 and the protruding portion 96 in the middle of the back span 91 of each M-shaped staple 90 move towards the inward recessed portions 69 of the ridge tops 65 of the oblique ridges 61 on the staple pockets 57 of the anvil 110, so as to bend the M-shaped staples 50 to form kidney-shaped staples 70 and bend the M-shaped staples 90 to form kidney-shaped staples 98. In this case, tips 117 of the legs 116 of the kidney-shaped staples 70 and tips 119 of the legs 118 of the kidney-shaped staples 98, which are adjacent and in two adjacent rings, are staggered relative to each other.

As shown in FIG. 14 to FIG. 18, FIG. 23 to FIG. 26, and FIG. 36 to FIG. 40, multiple staple pockets 57 are staggered-arranged in two rows on two sides of a cutter slot 121 on a tissue contacting surface of a linear anvil 120. M-shaped staples 50 and 90 arranged in a staple cartridge (not shown) correspond to positions of the staple pockets 57 arranged on the surface of the linear anvil 120. The M-shaped staples 50 are arranged on a far side of the cutter slot 121. The M-shaped staples 90 are arranged on a near side of the cutter slot 121. The degree in which the middle portion 96 of the back span 91 of each M-shaped staple 90 arranged on the near side of the cutter slot 121 of the linear anvil 120 protrudes towards the tips 94 and 95 of the two legs 92 and 93 is greater than the degree in which the middle portion 56 of the back span 51 of each M-shaped staple 50 arranged on the far side of the cutter slot 121 protrudes towards the tips 54 and 55 of the two legs 52 and 53. Extension lines of ridge lines of oblique ridges 124 and 125 of two adjacent staple pockets 122 and 123 in two adjacent rows intersect.

When staple drivers 126 push the M-shaped staples 50 and 90 out of a staple cartridge (not shown), the staple driver 126 urges the tips 54 and 55 of the two legs 52 and 53 of each M-shaped staple 50 and the tips 94 and 95 of the two legs 92 and 93 of each M-shaped staple 90 against the staple pockets 57 of the linear anvil 120, so that the two legs 52 and 53 of each M-shaped staple 50 and the two legs 92 and 93 of each M-shaped staple 90 bend along the staple guide lines 66 and 67 of the staple pockets 57 respectively, and meanwhile the protruding portion 56 in the middle of the back span 51 of each M-shaped staple 50 and the protruding portion 96 in the middle of the back span 91 of each M-shaped staple 90 move towards the inward recessed portions 69 of the ridge tops 65 of the oblique ridges 61 on the staple pockets 57 of the anvil 120, so as to bend the M-shaped staples 50 to form a kidney-shaped staples 70 and bend the M-shaped staples 90 to form a kidney-shaped staples 98. In this case, tips 128 of the legs 127 of the kidney-shaped staples 70 and tips 130 of the legs 129 of the kidney-shaped staples 98, which are adjacent and in two adjacent rows, are staggered relative to each other.

The processes of surgical staple and staple pocket for forming kidney-shaped staple according to a second embodiment of the present invention are described below with reference to FIG. 41 to FIG. 45, so as to illustrate effects of the surgical staple and staple pocket for forming kidney-shaped staple.

Figures 41, 42:
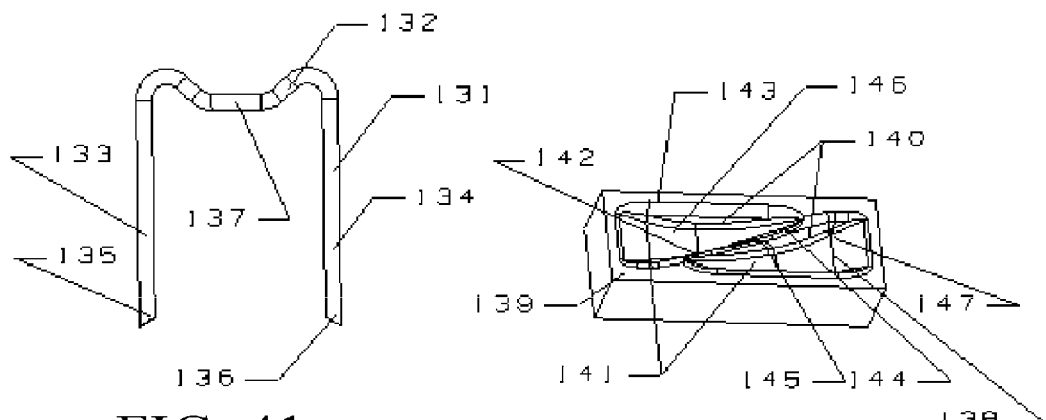
FIG. 41 is an outside view of an M-shaped staple according to a second embodiment of the present invention.
FIG. 42 is an outside view of a staple pocket for kidney-shaping an staple according to a second embodiment of the present invention.

As shown in FIG. 41, an staple 131 arranged in a staple cartridge (not shown) comprises a back span 132 and two legs 133 and 134. End portions of the two legs 133 and 134 of the staple 131 are provided with tips 135 and 136 respectively. Pointed ends of the tips 135 and 136 of the staple 131 are located on an outer side of the staple 131. A middle portion 137 of the back span 132 of the staple 131 protrudes towards the tips 135 and 136 of the two legs 133 and 134, so that the back span 132 and the two legs 133 and 134 of the staple 131 form an M-shaped staple 131.

A staple pocket 138 shown in FIG. 42 comprises a side surface 140, a bottom surface 141, and an oblique ridge 142 that are formed after inward recessing on a tissue contacting surface of a anvil 139. The staple pocket 138 forms perimeter 143 on the surface of the anvil 139. A ridge line of the oblique ridge 142 and a long axis of the staple pocket 138 intersect and form an acute angle. A ridge top 144 of the oblique ridge 142 is inward recessed towards the bottom surface 141. The oblique ridge 142 divides the bottom surface 141 into two parts. Intersection lines between the side surface 140 and the oblique ridge 142 of the staple pocket 138 and the bottom surface 141 form staple guide lines 146 and 147 of the staple pocket 138 respectively.

Figures 43, 44:
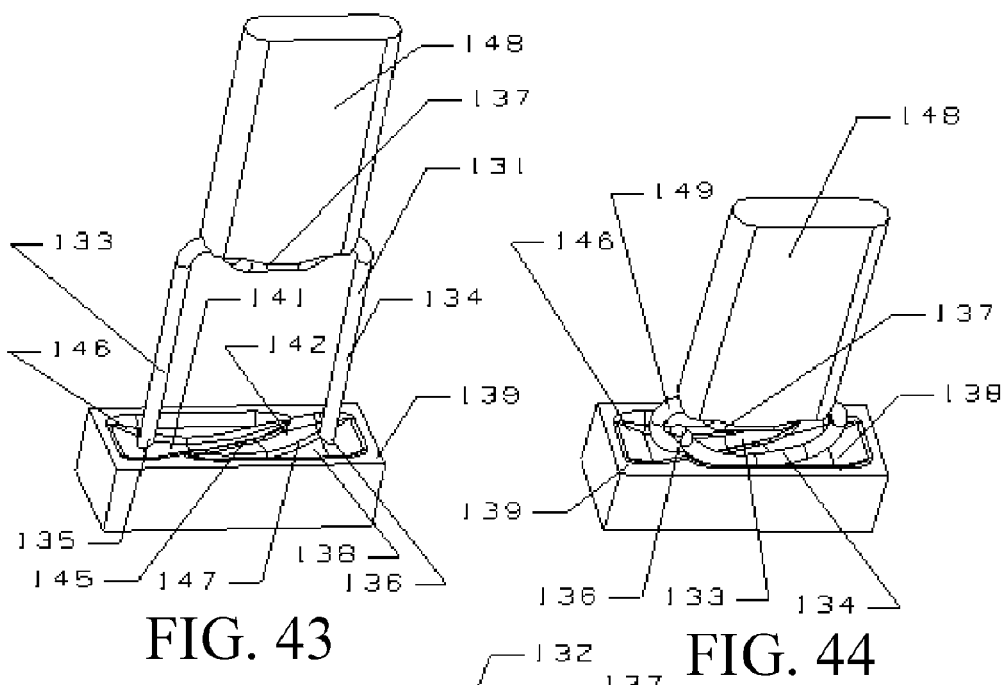
FIG. 43 is an outside view showing that a staple driver urges tips of an M-shaped staple against a staple pocket of a staple anvil.
FIG. 44 is an outside view showing that an M-shaped staple bends on a staple pocket of a staple anvil to form a kidney-shaped staple.
Figure 45:
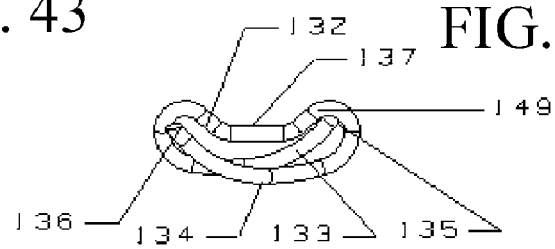
FIG. 45 is an outside view of a kidney-shaped staple shaped by bending.

As shown in FIG. 43 to FIG. 45, when a staple driver 148 pushes the M-shaped staple 131 out of a staple cartridge (not shown), the staple driver 148 urges tips 135 and 136 of the two legs 133 and 134 of the M-shaped staple 131 against the staple pocket 138 of the anvil 139, so that the two legs 133 and 134 of the M-shaped staple 131 bend along the staple guide lines 146 and 147 of the staple pocket 138 respectively, and meanwhile a protruding portion 137 in the middle of the back span 132 moves towards an inward recessed portion 145 of the ridge top 144 of the oblique ridge 142 on the staple pocket 138 of the anvil 139, so as to bend the M-shaped staple 131 to form a kidney-shaped staple 149.

The surgical staples and staple pockets for forming kidney-shaped staples in the present invention may be used in combination with surgical staples and staple pockets of another type according to surgical requirements on tissue stapling. For example, one ring or one row adopts the surgical staples and staple pockets for forming kidney-shaped staples in the present invention, and another ring or another row adopts surgical staples and staple pockets of another type.

It can be seen from the above detailed descriptions that, compared with the surgical staples and the staple pockets thereof in the various existing surgical staplers, the surgical staple and staple pocket for forming kidney-shaped staple in the present invention have the following technical effects.

In the surgical staple and staple pocket for forming kidney-shaped staple according to the present invention, when the M-shaped staple is bent to form a kidney-shaped staple, the two legs of the M-shaped staple cross each other and bend, so that the two tips deviate from the middle portion of the back span. Therefore, tissues to be stapled and varying in clamping thickness do not require staples having legs of different heights to be used, that is, the staple cartridge loaded with the M-shaped staples having the legs being the same in height is applicable to stapling tissues varying in clamping thickness. After the M-shaped staple is bent to form the kidney-shaped staple, the portion, in the middle of the back span of the M-shaped staple and protruding towards the tips of the two legs, protrudes into the crossing legs of the kidney-shaped staple, so that a spacing formed between the bent legs and the back span is narrow and long, the clamping force of the stapled tissue between the legs and the back span is distributed on the whole length of the back span, so as to achieve not only the surgical effect facilitating sealing and bleeding-stopping of the stapled tissue but also the surgical effect of facilitating healing of the surrounding tissue of the inner side of the edge of the stapled tissue, and achieve the use effect of making the use of the surgical stapler convenient and reducing the costs.

In the surgical staple and staple pocket for forming kidney-shaped staple according to the present invention, multiple staple pockets are staggered-arranged on two or more rings or in two or more rows on the tissue contacting surface of the staple anvil, and the positions of the M-shaped staples arranged in the staple cartridge correspond to the positions of the staple pockets on the surface of the staple anvil, so that after the M-shaped staples are bent to form the kidney-shaped staples, the kidney-shaped staples of two adjacent rows are staggered-arranged and can collectively block gaps between the staples, thereby achieving the surgical effect of facilitating sealing and bleeding-stopping of the stapled tissue. Further, the extension lines of the ridge lines of the oblique ridges of two adjacent staple pockets on two adjacent rings or in two adjacent rows intersect, so that after the M-shaped staples are bent to form the kidney-shaped staples, the positions of the tips of the legs of two adjacent kidney-shaped staples on the two adjacent ring or in the two adjacent rows are staggered relative to each other, so as to achieve not only the surgical effect of facilitating sealing and bleeding-stopping of the stapled tissue but also the surgical effect of enhancing the strength at the stapled tissue. If the degree in which the middle portion of the back span of the M-shaped staple arranged on the inner ring or on the near side of the cutter slot protrudes towards the tips of the two legs is greater than the degree in which the middle portion of the back span of the M-shaped staple arranged on the outer ring or on the far side of the cutter slot protrudes towards the tips of the two legs, when staples of the same height are used to staple stapled tissues varying in thickness, not only the surgical effect of facilitating sealing and bleeding-stopping of the edge of the stapled tissue can be achieved, but also the surgical effect of facilitating the healing of the surrounding tissue of the inner side of the edge of the stapled tissue can be achieved.

Therefore, it can be seen that the objectives, including the objectives shown by the above descriptions, are effectively achieved. Only typical and preferred embodiments of the present invention are described herein, and some changes may be made to the aforementioned structures without departing from the spirit and scope of the present invention. The present invention is not limited to or confined by the described specific details, and shall include, as stated in the claims, any improvement or modification obvious to persons of ordinary skill in the art.

What is claimed is:

1. A surgical staple and staple pocket for forming kidney-shaped staple, wherein:
   the staple is located in a staple cartridge, the staple comprises a back span and two legs, end portions of the two legs are provided with tips respectively, and a middle portion of the back span protrudes towards the tips of the two legs, so that the back span and the two legs of the staple form an M-shaped staple;
   the staple pocket comprises a side surface, a bottom surface, and an oblique ridge that are formed after the staple pocket is inward recessed on a tissue contacting surface of a staple anvil, the staple pocket forms perimeter on the surface of the staple anvil, a ridge line of the oblique ridge and a long axis of the staple pocket intersect and form an acute angle, a ridge top of the oblique ridge is inward recessed towards the bottom surface, the oblique ridge divides the bottom surface into two parts, and intersection lines between the side surface and the oblique ridge of the staple pocket and the bottom surface form staple guide lines of the staple pocket;
   when a staple driver pushes the M-shaped staple out of the staple cartridge, the staple driver urges the tips of the two legs of the M-shaped staple against the staple pocket of the staple anvil, so that the two legs of the M-shaped staple bend along the staple guide lines of the staple pocket respectively, wherein a portion, in the middle of the back span and protruding towards the tips of the two legs, moves towards a portion, inward recessed towards the bottom surface, of the ridge top of the oblique ridge on the staple pocket of the staple anvil, so as to bend the M-shaped staple to form a kidney-shaped staple;
   wherein, the staple anvil is circular, the multiple staple pockets are staggered-arranged on two or more rings on the tissue contacting surface of the circular staple anvil, and extension lines of ridge lines of oblique ridges of two adjacent staple pockets on two adjacent rings intersect.

2. The surgical staple and staple pocket for forming kidney-shaped staple as in claim 1, wherein the middle portion of the back span of the staple protrudes towards the tips of the two legs, and the axis of the back span comprises several curve segments, so that the back span and the two legs of the staple form the M-shaped staple.

3. The surgical staple and staple pocket for forming kidney-shaped staple as in claim 1, wherein the middle portion of the back span of the staple protrudes towards the tips of the two legs, and the axis of the back span comprises several straight line segments, so that the back span and the two legs of the staple form the M-shaped staple.

4. The surgical staple and staple pocket for forming kidney-shaped staple as in claim 1, wherein the middle portion of the back span of the staple protrudes towards the tips of the two legs, and the axis of the back span comprises curve segment and straight line segment, so that the back span and the two legs of the staple form the M-shaped staple.

5. The surgical staple and staple pocket for forming kidney-shaped staple as in claim 1, wherein the position of the M-shaped staple arranged in the staple cartridge and the position of the staple pocket on the surface of the circular staple anvil correspond to each other, and the M-shaped staple arranged on an inner ring has a greater degree convex which is towards tips of two legs and at a middle portion of the back span than the same the M-shaped staple arranged on an outer ring has.

6. The surgical staple and staple pocket for forming kidney-shaped staple as in claim 1, wherein the staple anvil is linear, and the multiple staple pockets are staggered-arranged in two or more rows on the tissue contacting surface of the linear staple anvil.

7. The surgical staple and staple pocket for forming kidney-shaped staple as in claim 6, wherein the linear staple anvil is provided with a cutter slot, and the multiple staple pockets are arranged on two sides of the cutter slot of the linear staple anvil.

8. The surgical staple and staple pocket for forming kidney-shaped staple as in claim 7, wherein the position of the M-shaped staple arranged in the staple cartridge and the position of the staple pocket on the surface of the linear staple anvil correspond to each other, and the M-shaped staple arranged near the cutter slot of the linear staple anvil has a greater degree convex which is towards tips of two legs and at a middle portion of the back span than the same the M-shaped staple arranged on a far side of the cutter slot has.

9. The surgical staple and staple pocket for forming kidney-shaped staple as in claim 6, wherein extension lines of ridge lines of oblique ridges of two adjacent staple pockets on two adjacent rows intersect.

10. The surgical staple and staple pocket for forming kidney-shaped staple as in claim 1, wherein the staple comprises a back span and two legs, end portions of the two legs of the staple are provided with tips respectively, pointed ends of the tips of the staple are located on an outer side of the staple, and a middle portion of the back span of the staple protrudes towards the tips of the two legs, so that the back span and the two legs of the staple form an M-shaped staple.

11. The surgical staple and staple pocket for forming kidney-shaped staple as in claim 1, wherein the staple comprises a back span and two legs, end portions of the two legs of the staple are provided with tips respectively, pointed ends of the tips of the staple are located on an inner side of the staple, and a middle portion of the back span of the staple protrudes towards the tips of the two legs, so that the back span and the two legs of the staple form an M-shaped staple.

* * * * *